(12) United States Patent
Scheve et al.

(10) Patent No.: US 12,024,677 B2
(45) Date of Patent: Jul. 2, 2024

(54) METHODS AND SYSTEMS FOR USE OF QUATERNARY AMMONIUM ORGANOSILANES IN OIL AND GAS HYDRAULIC FRACKING

(71) Applicant: Nano Global Corporation, Austin, TX (US)

(72) Inventors: Christine Scheve, Austin, TX (US); William Peterson, III, Austin, TX (US); Zoltan Papp, Austin, TX (US); Steven Papermaster, Austin, TX (US); Stephen Smid, Austin, TX (US)

(73) Assignee: Nano Global Corporation, Austin, TX (US)

( * ) Notice: Subject to any disclaimer, the term of this patent is extended or adjusted under 35 U.S.C. 154(b) by 111 days.

(21) Appl. No.: 16/638,287

(22) PCT Filed: Aug. 10, 2018

(86) PCT No.: PCT/US2018/046213
§ 371 (c)(1),
(2) Date: Mar. 12, 2020

(87) PCT Pub. No.: WO2019/032963
PCT Pub. Date: Feb. 14, 2019

(65) Prior Publication Data
US 2021/0317361 A1 Oct. 14, 2021

Related U.S. Application Data

(60) Provisional application No. 62/544,301, filed on Aug. 11, 2017.

(51) Int. Cl.
| E21B 43/267 | (2006.01) |
| C02F 1/00 | (2023.01) |

(Continued)

(52) U.S. Cl.
CPC .............. *C09K 8/605* (2013.01); *C02F 1/004* (2013.01); *C02F 1/50* (2013.01); *C09K 8/22* (2013.01);
(Continued)

(58) Field of Classification Search
CPC ....................................................... E21B 43/26
See application file for complete search history.

(56) References Cited

U.S. PATENT DOCUMENTS

2015/0321924 A1* 11/2015 Wrubel ................... C02F 1/22
62/532
2015/0336808 A1 11/2015 Soane et al.
(Continued)

FOREIGN PATENT DOCUMENTS

| WO | WO1992014810 A1 | 9/1992 |
| WO | WO2015076785 A1 | 5/2015 |

OTHER PUBLICATIONS

Christine Scheve, International Search Report for PCT/US2018/046213, dated Oct. 22, 2018.

*Primary Examiner* — William D Hutton, Jr.
*Assistant Examiner* — Avi T Skaist
(74) *Attorney, Agent, or Firm* — Terrile, Cannatti & Chambers, LLP; Emmanuel A. Rivera

(57) ABSTRACT

The technology described herein includes methods and uses in oil and gas hydraulic fracking for a quaternary ammonium organosilane, and particularly AMOSILQ™ quaternary ammonium organosilane. Uses include coating and treating filters for use in the hydraulic fracking process, premixing in fracking fluid/water; flowback water treatment and proppant coating.

7 Claims, 1 Drawing Sheet

(51) Int. Cl.
*C02F 1/50* (2023.01)
*C09K 8/22* (2006.01)
*C09K 8/60* (2006.01)
*C09K 8/68* (2006.01)
*C09K 8/80* (2006.01)
*E21B 43/40* (2006.01)
*C02F 103/10* (2006.01)

(52) U.S. Cl.
CPC ................ *C09K 8/68* (2013.01); *C09K 8/805* (2013.01); *E21B 43/267* (2013.01); *E21B 43/40* (2013.01); *C02F 2103/10* (2013.01); *C02F 2303/04* (2013.01)

(56) References Cited

U.S. PATENT DOCUMENTS

| | | |
|---|---|---|
| 2016/0200965 A1 | 7/2016 | Farion et al. |
| 2016/0355487 A1 | 12/2016 | Huigens, III et al. |
| 2017/0073253 A1 | 3/2017 | Peterson, III et al. |

* cited by examiner

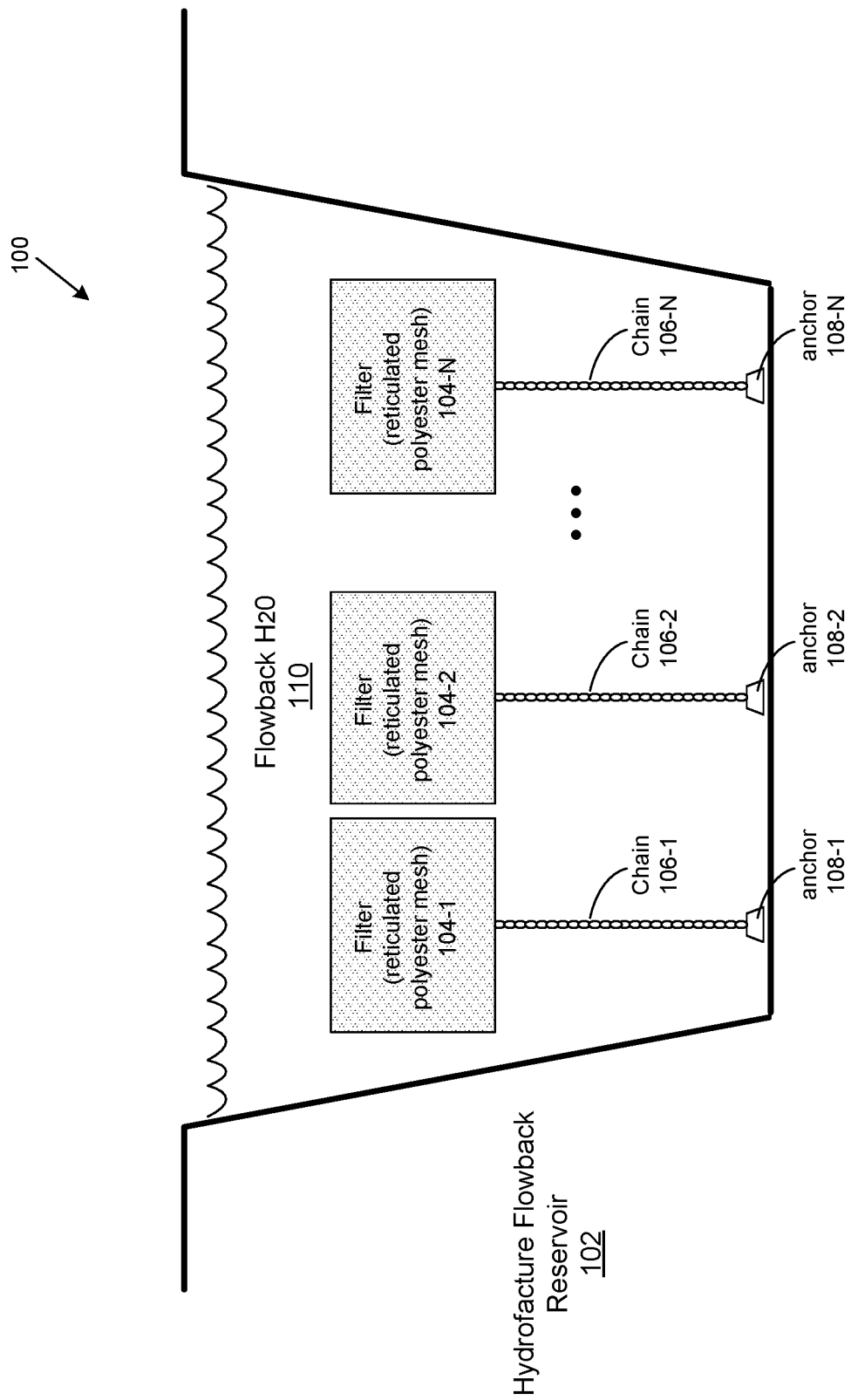

METHODS AND SYSTEMS FOR USE OF QUATERNARY AMMONIUM ORGANOSILANES IN OIL AND GAS HYDRAULIC FRACKING

RELATED APPLICATIONS

This application claims the benefit of priority of U.S. Provisional Patent Application Ser. No. 62/544,301 filed Aug. 11, 2017, incorporated herein by reference.

BACKGROUND

Hydraulic fracturing or fracking is the process of injecting liquid at high pressure into subterranean rocks, boreholes to force open existing fissures and extract oil or gas. Hydraulic fracturing, as the term implies, involves water, at the front end with fracking fluid, a water-based chemical solution injected into shale, and at the back end where there is flowback water and produced water. Fracking fluid is a chemical mixture used in drilling operations to increase the quantity of hydrocarbons that can be extracted.

Drilling mud may be defined as a drilling fluid used in drilling engineering. The drilling mud may be composed of oil as the continuous phase and water as the dispersed phase in conjunction with emulsifiers, wetting agents and gellants. The oil base can be diesel, kerosene, fuel oil, selected crude oil or mineral oil. Drilling mud can also refer to the hole/well or mud from the drilling hole. Slick water or slick water fracturing, is a method or system of fracking which involves adding chemicals to water to increase the fluid flow.

Flowback water, or backflow water, is the murky, salty water from fracking natural gas wells. Flowback water includes fracking fluid which returns to the surface, known as the fracking load recovery, as well as produced water. This water contains clay, dirt, metals, chemicals and even the oil based additives. Flowback water may be characterized as having high salinity and total dissolved solids (TDS). It is laden with the same fracking chemicals that were pumped into the well, in addition to any unique contaminants that are present in the rock formation water deep below. In addition to natural salinity of water in the formation, any fresh water that is forced down a well, when it is fracked, will tend to dissolve salts in the formation thus giving the recovered water very high salinity.

The returning fluid is generally collected in metal tanks or else open pools, lagoons or pits lined with one or more layers of plastic. These receptacles may be pumped dry, and water is usually either recycled for fracking additional wells or else trucked off site to a waste water disposal facility. Containment pits, or open-air ponds that are lined with plastic, can become points of failure. Occasionally, liners get cracked or damaged. Contaminated fluids can then leach into ground water.

When fracking is performed, biocides such as glutaraldehyde may be added to the high-pressure water that is used. Such biocides are used as a preventive against bacteria and microbes that produce hydrogen sulfide, which can corrode pipelines and damage equipment. Bacteria may cause bioclogging and inhibit gas extraction, produce toxic hydrogen sulfide, and induce corrosion leading equipment failure. In many instances, the use of stainless steel pipes is implemented to protect against the hydrogen sulfide produced by microbes/bacteria.

The use of biocides, such as glutaraldehyde compounds, can have negative implications, such as inadvertent releases into the environment on ecosystem and human health. For example, uncharged species can dominate in the aqueous phase and be subject to degradation and transport whereas charged species will sorb to soils and be less bioavailable. Biocides may transform into more toxic or persistent compounds. Currently there is limited understanding as to biocides' long term effects under downhole conditions, such as high pressure, temperature, and salt and organic matter concentrations. Biocides alternatives may be costly, have high energy demands, and/or are not as effective.

Proppants are a key components in fracking. A proppant may be a solid material, typically sand, treated sand, or man-made ceramic materials, designed to keep an induced hydraulic fracture open, during or following a fracturing treatment. Sand may degrade from corrosion due to bacteria and microbes.

BRIEF DESCRIPTION OF THE DRAWINGS

The detailed description is described with reference to accompanying FIGURES. In the FIGURES, the left-most digit(s) of a reference number identifies the FIGURE in which the reference number first appears. The same numbers are used throughout the drawings to reference like features and components.

FIG. 1 is an example system for treatment of hydrofracturing flowback water for reuse.

DETAILED DESCRIPTION

Described herein are uses, systems and methods for the use of a quaternary ammonium organosilanes in hydraulic fracturing or fracking. In certain implementations, for example, octadecyldimethyl (3-trihydroxypropyl) ammonium chloride, or the AMOSILQ™ "quaternary ammonium organosilane" is used. It is to be understood that other molecular compounds of quaternary ammonium organosilanes may be used. In particular, quaternary ammonium compounds that are silated or in the silane group. Such silated quaternary ammonium compounds, and in particularly quaternary ammonium organosilane molecules are in a monomer form, and have linkers to allow binding and polymerization to surfaces such as fracking equipment and proppants. Furthermore, quaternary ammonium organosilanes have a property that creates a covalent bond with surfaces that aligns quaternary ammonium organosilane molecules to effectively kill bacteria and microbes. In effect, forming a very robust surface barrier against bacteria and microbes.

Environmental effects evident with current biocides, include biocides leaching into and negatively affecting the environment. Quaternary ammonium organosilanes that are polymerized with surfaces, sloths over time into safer organic constituents into the environment. Furthermore, it may be more cost efficient using quaternary ammonium organosilanes in place of certain biocides.

Quaternary ammonium organosilanes may also be used to strengthen proppants. Sand can degrade from corrosion caused by bacteria and microbes. Unlike other biocides, quaternary ammonium organosilane binds with proppants such as sand to kill bacteria and microbes. This effectively prolongs the useful life of the proppant, and creates a static antimicrobial component. Since sand is porous, the quaternary ammonium organosilane molecules are able to soak into sand. As the proppant breaks down, quaternary ammonium organosilane molecules continue to provide antimicrobial efficacy. Quaternary ammonium organosilanes can have a longer efficacy than biocides.

Quaternary ammonium organosilanes, for example AMOSILQ™ quaternary ammonium organosilane, may be used throughout the fracking process, at different phases. For example adding quaternary ammonium organosilanes into fracking fluid, including static water and slick water, adding into flow back water, coating proppants, etc. Quaternary ammonium organosilanes may be also used to coat proppants, such as solids, sand, treated sand, ceramics, etc. Quaternary ammonium organosilanes may be used to replace and eliminate certain chemicals, such as biocides that are used as preemptive measures against bacteria and microbes.

The use of quaternary ammonium organosilanes in the fracking process may result in the reduction of water used to flush biocides and corrosive bacteria; reduction of energy use associated with water usage; reduction/elimination of toxic biocide usage; and environmental benefits in reducing/eliminating toxic biocides, reduced water use and efficient fracking.

Quaternary Ammonium Organosilanes in Fracking Fluid/Water

Quaternary ammonium organosilanes may be mixed in with fracking fluid or water. An appropriate concentration is determined to prevent film forming that can hinder fracking process. This concentration may approximately be 5 percent stabilized in water. Feasible concentrations may range from one percent to 50 percent soluble in water. In replacing biocides, advantages can include an increase microorganism kill rate over current biocides, enhanced biofilm prevention, prolonged kill rate through lifespan of drilling mud/hole. The quaternary ammonium organosilanes have the ability to attach to constituents. Quaternary ammonium organosilanes are stable with minimum impact to drilling in mud component functionality. Quaternary ammonium organosilanes are stable in extreme fracking environments, such as heat and pressure. Quaternary ammonium organosilanes are stable in in monomer and bound (polymerized) forms. A quaternary ammonium organosilane molecule is a monomer, and will polymerize with contact on substrates and surfaces. A quaternary ammonium organosilanes mixed in with fracking fluid can polymerize with different substrates and surfaces. Quaternary ammonium organosilanes can coat equipment, pipes, casing, etc., providing microbial kill, biofilm prevention. Quaternary ammonium organosilanes can have increased disinfectant rates in pressure and temperature over biocides. In addition, AMOSILQ™ quaternary ammonium organosilane is rated by the EPA as chemical/category 4.

Quaternary Ammonium Organosilane as Coating

As described above, a quaternary ammonium organosilane in solution, such a fracking fluid, is a monomer, and can polymerize with coatings and surfaces, such as those on fracking equipment. Benefits include the ability to use less expensive material that is more susceptible to corrosion, such as the use of carbonated steel in place of stainless steel for pipes.

Quaternary ammonium organosilane in a fluid, can be an indirect method of coating such equipment. Direct methods may also be implemented in coating equipment with quaternary ammonium organosilane. The use of quaternary ammonium organosilane as coating for equipment can lead to more efficient microbial kill and biofilm prevention.

Quaternary Ammonium Organosilane in Water Treatment

The use of quaternary ammonium organosilanes may be used in coating water purification systems, such as systems that treat flowback water. Such use can lead to more efficient microbial kill and biofilm prevention. Quaternary ammonium organosilane in solution can be used in static water, fracking fluid/water, and flowback water. Quaternary ammonium organosilanes may be used in high pressure situations, including static systems. High pressure can involve 1000 gallons per minute or 100 psi. Quaternary ammonium organosilanes may be added and used in fracking tanks before and after the fracking process(es). Fracking tanks may harbor harmful bacteria and microbes. Such fracking tanks may be portable and transportable on trucks. Such tanks may be 1000 lbs and have four chambers. Water lines in water purification systems, including those to water tanks, may be approximately eight inches in diameter. In certain implementations, different gravel/meshes are used in fracking tanks. The gravel/meshes can be treated with quaternary ammonium organosilane to kill microbes and bacteria. Such quaternary ammonium organosilane based gravel/meshes can replace current foam meshes that have a more limited use.

FIG. 1 shows a system 100 for treatment of hydrofracturing flowback water for reuse. Water is a major component in hydraulic fracking, and is a scarce resource. Considering the relatively large amount of water that is needed in hydraulic fracking, transportation costs are significant. Therefore, there is a great interest in efficient use of water, such as reuse in hydraulic fracking.

A major problem with water recycling or reuse process is bacterial and microbial populations that come back with the flowback water. The storage time the water sits in earthen pits also proliferates high bacterial populations. Flowback water can contain a type of bacteria called an SRB (Sulfate reducing bacteria). This bacteria basically reduces sulfate to hydrogen sulfide. Hydrogen sulfide on its own can be very dangerous, and can turn the flowback water to sulfuric acid. The MIC (microbial induced corrosion) causes billions of dollars in damage to equipment every year. Therefore, biocides are typically used in oil-water separation units, water storage tanks, and pipelines used to transport fluids. However, as discussed, biocides can have negative effects. As discussed, quaternary ammonium organosilane coatings may be used to help reduce the impact of corrosion and scale within the hydrofracturing equipment and piping.

Now in reference to FIG. 1, in a first stage, large blocks coated with quaternary ammonium organosilane material, such as WaterQore™ are anchored down into flowback reservoirs to start the job of disinfecting bacteria. The system 100 may make use low powered driven (e.g., solar powered) larger PPI (pores per inch) reticulated mesh "paddles" that would slowly turn and agitate possibly increasing disinfection time.

In a second stage, a sand filtration system can be used. Water tanks can be filled with quaternary ammonium organosilane coated sand at different mesh sizes. There is also a possibility of using different materials to treat the total dissolved solids and heavy metal content in the primary filtration stage. This high pressure step can also address high-pressure wastewater and drinking water applications using a combination of sand and cartridge systems.

With these two systems we could eliminate bacteria from flowback water providing an inexpensive and efficient way to reuse flowback water with much less environmental impact. The systems could also be used to treat topside fracking water before use, in transport vehicles, and storage tanks to disinfect the water before use to improve efficiency and production.

Quaternary Ammonium Organosilane in Proppants

As discussed above, quaternary ammonium organosilanes may be used for proppants in the fracking process. Quaternary ammonium organosilane coated proppants can provide static cleaning without pressurization. Quaternary ammonium organosilanes dry on their own.

As discussed, quaternary ammonium organosilanes can strengthen proppants. For example, sand can degrade from corrosion caused by bacteria and microbes. Unlike other biocides, quaternary ammonium organosilane binds with proppants such as sand to kill bacteria and microbes, and effectively prolongs the useful life of the proppant, and creates a static antimicrobial component. Since sand is porous, the quaternary ammonium organosilane molecules are able to soak into the sand. As the proppant or sand breaks down, quaternary ammonium organosilane molecules continue to provide antimicrobial efficacy. Quaternary ammonium organosilanes can have a longer efficacy than biocides.

In certain implementations, the proppants may already be placed downhole in shale in the fracking process. Coating of such proppants with quaternary ammonium organosilanes may be performed using what is commonly referred to in the industry as a "frack pack." In such cases, for example, a line may be used to directly apply concentrated quaternary ammonium organosilanes to proppants that are in place (i.e., in the shale).

What is claimed is:

1. A system for reusing water in a hydraulic fracking process, the system comprising:
   a primary stage that comprises:
      a flowback reservoir of a fracking well to receive hydrofracturing flowback water for reuse in the fracking well, wherein quaternary ammonium organosilane is added to the hydrofracturing flowback water and proppants;
      mesh blocks that are configured as filters in the flowback reservoir, wherein the mesh blocks are coated with quaternary ammonium organosilane that is combined with the hydrofracturing flowback water in solution, wherein the quaternary ammonium organosilane is polymerized to the surfaces of the mesh blocks; and
      reticulated paddles; and
   a secondary stage that comprises:
      water tanks with quaternary ammonium organosilane coated sand at different mesh sizes to receive dissolved solids and heavy metal content of the primary stage.

2. The system of claim 1, wherein the mesh blocks are part of a tank or tanks for storing hydraulic fracking water.

3. The system of claim 1, wherein the quaternary ammonium organosilane is five percent soluble in water.

4. The system of claim 1, wherein the quaternary ammonium organosilane is one to 50 percent soluble in water.

5. The system of claim 1, wherein the fracking fluid is drilling mud.

6. The system of claim 1, further comprising coating fracking equipment and constituents in the hydraulic fracking process with the quaternary ammonium organosilane.

7. The system of claim 1, wherein the percentage of quaternary ammonium organosilane is determined based on possible biofilm buildup on fracking equipment.

* * * * *